(12) United States Patent
Furue et al.

(10) Patent No.: US 8,725,229 B2
(45) Date of Patent: May 13, 2014

(54) COVER SHEET FOR A BODY MEASURING APPARATUS AND AN AUTOMATIC SHEET DISPENSER THEREFOR

(75) Inventors: Masaaki Furue, Tokyo (JP); Minoru Ogura, Tokyo (JP); Makoto Niizato, Tokyo (JP); Kazuaki Natsume, Tokyo (JP)

(73) Assignee: Tanita Corporation, Tokyo (JP)

( * ) Notice: Subject to any disclaimer, the term of this patent is extended or adjusted under 35 U.S.C. 154(b) by 813 days.

(21) Appl. No.: 12/032,073

(22) Filed: Feb. 15, 2008

(65) Prior Publication Data

US 2008/0200793 A1 Aug. 21, 2008

(30) Foreign Application Priority Data

Feb. 15, 2007 (JP) ................................ 2007-034782
Nov. 20, 2007 (JP) ................................ 2007-300859

(51) Int. Cl.
*A61B 5/05* (2006.01)

(52) U.S. Cl.
USPC ............ 600/393; 600/547; 600/384; 439/909

(58) Field of Classification Search
USPC ................... 600/372, 382, 547, 393; 439/909
See application file for complete search history.

(56) References Cited

U.S. PATENT DOCUMENTS

| | | | | |
|---|---|---|---|---|
| 2,943,628 A | * | 7/1960 | Howell | 600/391 |
| 3,367,851 A | * | 2/1968 | Filreis et al. | 205/52 |
| 3,811,523 A | * | 5/1974 | Artwick et al. | 177/180 |
| 4,543,958 A | * | 10/1985 | Cartmell | 600/391 |
| 4,779,630 A | * | 10/1988 | Scharnberg et al. | 607/142 |
| 5,534,346 A | * | 7/1996 | Robinson | 428/343 |
| 5,842,985 A | * | 12/1998 | Lundback | 600/387 |
| 5,891,028 A | * | 4/1999 | Lundback | 600/387 |
| 6,055,452 A | * | 4/2000 | Pearlman | 600/547 |
| 6,115,638 A | * | 9/2000 | Groenke | 607/142 |
| 6,694,193 B2 | * | 2/2004 | Jonsen et al. | 607/142 |

(Continued)

FOREIGN PATENT DOCUMENTS

| | | | | |
|---|---|---|---|---|
| JP | 09313456 A | * | 12/1997 | |
| JP | 11128198 A | * | 5/1999 | |
| WO | WO 9302616 A1 | * | 2/1993 | |

OTHER PUBLICATIONS

Medical Supplies & Equipment Company sales webpage for "Hausmann Pediatric Table" (page dated Oct. 2006; accessed via internet archive Nov. 2011).*
Medical Supplies & Equipment Company sales webpage for "Banta/Tidi Exam Rolls, Crepe—14 in×125 ft" (page dated Oct. 2006; accessed via internet archive Nov. 2011).*

*Primary Examiner* — Linda Dvorak
*Assistant Examiner* — Erin M Cardinal
(74) *Attorney, Agent, or Firm* — Young & Thompson (57) ABSTRACT

A cover sheet (1) used in a body measuring apparatus having electrodes for supplying current to a human body or for measuring a difference in electrical potential between two sites of the body. The cover sheet has electric conductive area portions (2) corresponding to the electrodes of the body measuring apparatus and having a electric conductivity in thickness direction, and insulation area portions (3) spacing adjacent electric conductive area portions (2) and having electrically insulating property at least along a plane direction. The cover sheet is used to prevent cross-infection and can be used safely without slip and prepared cheaply without affecting to impedance, with assuring completely insulation between adjacent electrodes. Conductivity is created with conductive solid ("dry type") or conductive liquid ("wet type"). The cover sheet is fed automatically by a sheet dispenser.

18 Claims, 7 Drawing Sheets

(56) References Cited

U.S. PATENT DOCUMENTS

| | | |
|---|---|---|
| 7,009,119 B2 * | 3/2006 | Carlucci et al. ............... 177/199 |
| 7,162,291 B1 * | 1/2007 | Nachaliel ...................... 600/393 |
| 2001/0023878 A1 * | 9/2001 | Irwin ........................... 222/192 |
| 2002/0026229 A1 * | 2/2002 | Weil et al. ..................... 607/142 |
| 2002/0072687 A1 * | 6/2002 | Hakomori et al. ............. 600/547 |
| 2007/0038140 A1 * | 2/2007 | Masuo et al. .................. 600/547 |
| 2010/0081913 A1 * | 4/2010 | Cross et al. ................... 600/386 |

\* cited by examiner

COVER SHEET FOR A BODY MEASURING APPARATUS AND AN AUTOMATIC SHEET DISPENSER THEREFOR

BACKGROUND OF THE INVENTION

1. Field of the Invention

This invention relates to a cover sheet used in a live body measuring apparatus or in a weigh-measuring unit equipped with electrodes for supplying electric current to a live body and/or for measuring a potential difference between two sites of the live body.

More particularly, this invention relates to a cover sheet used in a "body composition measuring apparatus" for measuring body impedance using a body impedance technique, and an automatic dispenser of the cover sheets.

This invention further relates to a "cover sheet stock" comprising a plurality of unit cover sheets connected or stacked one another in separable manner, and a set or combination of the cover sheet stock and an openable container such as bag and case for storing the cover sheet stock hermetically.

2. Description of Related Arts

The "body composition measuring apparatus" is known for calculating an amount of internal fat or other information concerning body composition and/or structure from detected impedance between two sites of the body (i.e. between distal areas) and from body conditions such as body height and body weight. Applicant Company produces and commercializes a variety of body composition measuring apparatus. The mechanism of such body composition measuring apparatus is disclosed in many documents such as JP-A1-05-49050 (now Japanese Patent No. 1848283).

The principle of the body composition measuring using the impedance technique in which a difference in electric inductivity on different parts of a body composition is measured is disclosed in following documents: Keisoku Gijutsu, "Measuring Technique", September, 2004, p. 14-20 and Nihon Rinsyo, Vol. 53, 1995 special edition, Jun. 22, 1995, p. 179-182. The contents of documents listed above consist part of this specification.

In mass physical checkup or health examination in which a great number of unnamed persons use a same body composition measuring apparatus or a weigh-measuring unit one after another, it is advisable to take a precaution against a cross infection. In such body composition measuring apparatus or the weigh-measuring unit, an examinee stands thereon barefoot, so that a danger of cross infection increase.

Still more, a body composition measuring apparatus using impedance technique is sensitively affected by the body status (biological variability) of examinee as described in above documents. Therefore, it is advisable to avoid such situation that the examinees feel discomfort or panic. In case of a mass physical checkup or a complete medical checkup which force many examinees to be measured by turns, several examinees feel hesitated to use the same measuring apparatus just after other examinee used it. In light of this, it is beneficial or advantageous to let the examinees know cleanness of the measuring apparatus to obtain a proper measuring result.

Above-mentioned problem may not be so serious in case of home uses. However, there is a need to use a cover sheet for the measuring apparatus as an etiquette sheet when a visitor such as friends and relatives comes and uses a body composition measuring apparatus or the weigh-measuring unit under a cleaned condition.

By wiping its platform, a surface the measuring apparatus could be kept clean. In case of the mass physical checkup or complete medical checkup, however, it needs to be kept cleaned up by an operator. Moreover, water left non-uniformly on a surface of a measuring unit may cause an error in measuring. It is not easy to keep its surface clean by simple means in such measuring apparatus as an internal fat meter in which a delicate difference in electric conductivity of body composition is measured.

The platform of the measuring apparatus may be covered by a simple cover sheet. The platform of a body composition measuring apparatus, however, has a plurality of electrodes (generally two or four electrodes) and these electrodes must be electrically isolated each other. Covering materials that give influence to impedance cannot be selected. Moreover, it could never be allowed that an examinee, for example an old person, slips and get injured during its use. Furthermore, costly methods or materials are not acceptable in practical uses.

An object of the present invention is to provide a cover sheet for a body composition measuring apparatus using the impedance technique, which can prevent a cross injunction, which can be used safely, without giving serious influence to impedance to be measured, which can assure isolation between cathodes, and which can be used at low cost.

Another object of the present invention is to provide a disposal cover sheet made of non-woven web optionally having anti-slip treatment on at least part thereof, which is placed, in use, on a face of a weigh-measuring unit.

Still another object of this invention is to provide a cover sheet stock comprising a plurality of unit cover sheets connected or stacked one another in separable manner, and a set or combination of the stock and an openable container in which the stock is stored hermetically.

Still another object of this invention is to provide an automatic cover sheet dispenser for feeding and setting the cover sheet onto electrode portions of a live body measuring apparatus automatically.

SUMMARY OF THE INVENTION

A first subject of the present invention resides in a cover sheet used in a body measuring apparatus having electrodes for supplying current to a human body or for measuring a difference in electrical potential between two sites of the body, in which the cover sheet has electric conductive area portions corresponding to the electrodes of the body measuring apparatus and having a electric conductivity in thickness direction, and insulation area portions spacing adjacent electric conductive area portions and having electrically insulating property at least along a plane direction.

In an example of this invention, the electric conductivity in thickness direction is created by dispersion, adhesion or addition of electro-conductive solid material into and/or onto a sheet material (this case is called hereinafter, "dry type"). This electro-conductive solid material may be electro-conductive particles, powder or fibers.

In an example of this invention, the electric conductivity in thickness direction is created by impregnation, adhesion or absorption of electro-conductive liquid into and/or onto a sheet material (this type is called hereinafter, "wet type"). This electro-conductive liquid may be an electro-conductive aqueous solution.

The "dry type" and the "wet type" can be used in combination. For example, a "dray type" cover sheet may be coated with electro-conductive aqueous solution such as water.

The sheet material may be in a form of non-woven web or textile, fiber web, felt, woven textile, knitting or film.

The cover sheet according to the present invention has preferably anti-slip means arranged on at least part of an upper surface and/or a lower face thereof.

The electric conductive area portions may be located at positions corresponding to electrode portions that contact with feet bottom of an examinee on a platform of a body composition measuring apparatus or with hands of the examinee.

The cover sheet according to this invention may be made of non-woven web and can be disposal. The electric conductive area portions may be prepared by electro-conductive treatment.

A second subject of this invention resides in a disposal cover sheet made of a non-woven web and having at least partly anti-slip treatment.

A third subject of this invention resides in a stock of the cover sheet, comprising a plurality of unit cover sheets connected in series in separable manner, each unit cover sheet comprising electric conductive area portions corresponding to said electrodes of said body measuring apparatus and having a electric conductivity in thickness direction, and insulation area portions spacing adjacent electric conductive area portions and having electrically insulating property at least along a plane direction. A preferable form of the stock is a roll form. The stock can be made of a plurality of stacked unit cover sheets. In this case, it is preferable to nest two unit cover sheets partly successive so that the unit cover sheets can be withdrawn continuously like so-called. "tissue paper" stack in a box.

A forth subject of this invention resides a set of the stock of the wet type cover sheet and an open-able container packing the stock hermetically. This set is advantageous to prevent evaporation of the electro-conductive liquid during use or storage, when the electric conductivity in thickness direction is created by impregnation, adhesion or absorption of electro-conductive liquid into and/or onto a sheet material. In particular, this set can be used in home uses to store of the wet type cover sheets.

A fifth subject of this invention resides an automatic cover-sheet dispenser, comprising a feeding unit of the cover sheet arranged at a side of the electrodes of said body measuring apparatus, and a collecting unit of the cover sheet which can be arranged at opposite side or even at the same side as the feeding unit. The automatic cover-sheet dispenser is particularly advantageous in such a case that many examinees are measured successively in a health center, hospital and complete physical examination. The cover sheet can be fed from a cover sheet stock in a form a roll or stack.

The automatic cover-sheet dispenser may have a feeder of electro-conductive liquid. The electric conductive area portions of a cover sheet can be impregnated, adhered or absorbed with the electro-conductive liquid by passing the cover sheet through a bath containing the electro-conductive liquid. The electro-conductive liquid can be fed also by a sponge roll through which water is fed continuously, or can be sprayed.

DESCRIPTION OF THE PREFERRED EMBODIMENTS

"A body composition measuring apparatus" is understood as a measuring apparatus that calculates the information of a body composition and structure (such as amount of fat) from impedance between two portions of a body and from physical conditions such as body height and body weight.

"A thickness direction" is understood as a direction from a surface to an opposite surface of the cover sheet, and "plane direction" is understood as a direction that is in parallel to or almost parallel to the surfaces.

Expression of "has a electric conductivity" means literally having a property of electric conductivity. Ideally condition is zero electric resistance but it is possible to have a certain degree of electric resistance. In any way, the electric resistance is desirably homogeneous throughout the electric conductive area portions.

Expression of "having at least partly anti-slip treatment" is understood as such anti-slip treatment as not affecting the measured results in a body composition measuring apparatus using the body impedance.

The measured valued obtained by a body composition measuring apparatus may be corrected by using a calibration table or curve.

The "electro-conductive solid" is understood as electro-conductive particles or powder which is solid at usage, such metal powder of aluminum, iron, silver and gold or of metal salt or inorganic powder such as carbon powder, metal fibers or carbon fibers. Carbon nanotubes also can be used. In general, the electro-conductive solid is added to a sheet material such as non-woven web, fiber web and felt at a preparation stage of the cover sheet, or the electro-conductive solid is kneaded into fibers during a stage when the fibers are prepared, or the electro-conductive solid is applied, penetrated or dispersed onto a surface of the cover sheet or into the cover sheet, to create the electric conductivity in thickness direction.

The "electro-conductive liquid" is understood as electro-conductive liquid that is liquid state at usage and is usually aqueous solution. The electro-conductive liquid can be tap water (usually containing chloride). Water can be added with suitable substances that can increase the electro-conductivity, and/or, that can create uniform electro-conductivity, such as agent for generating electro-conductive ions such as water-soluble salts such as sodium chloride. The aqueous solution may contain agents that can avoid or retard desiccation such as humectants, wetting agent and dry resistance agent such as acryl amide, polyvinyl acetoamimde, polyalkylene glycol esters. The aqueous solution may contain other additives such as antibacterial agent, disinfectant, anti-microbial agent, deodorant, antioxidant, moisture retaining agent, additives having a variety of functions such as relaxation, freshness, anti-phlogistic and analgesic properties, catechin possessing many actions contributing to health and beauty such as anti-fungus, anti-allergic, humidity retention, environment atmosphere improvement and aromatherapy actions, and additives such as sterilization ceramics and borax, photo-catalysts such as titania, antioxidants, flame retardants or the like.

Expression of "having an anti-slip character" is understood as such a condition that the cover sheet does not slide on the body measuring apparatus or on a weigh-measuring unit, even when a aged person of the largest danger in injury uses the body measuring apparatus or the weigh-measuring unit.

The cover sheet according to this invention is preferably prepared from non-woven web or textile from the viewpoint of strength, insulation, hygiene, safety and cost. Non-woven web is a well-known material and variety types of non-woven webs are sold on market. Non-woven web can be produced by a variety of methods and from a variety of materials. The materials may be natural fiber such as fibers of cotton, hemp or bamboo, animal fibers such as sheep wool, silk, chemical fiber such as rayon, cupra, acetate, polyamide, polyester, polyacrylonitrile, polyvinyl alcohol, polyolefin such as polyethylene, polypropylene, polyvinylidene chloride and polyurethane, inorganic fiber such as glass fiber, metallic fibers and carbon fibers. The method for producing non-woven webs also is not specially limited and can be used any known technique such as adhesive method, thermal bond method, ultrasonic wave adhesive method, needle punch method, span lace method, stitch bond method, span bond method, melt blow method, centrifugal force method, flash spin method, voltage dry spin method, film method, air lay method, guard method and garneting machine method.

The cover sheet according to the invention is preferably disposal type, since the production cost is mostly important. In light of this, it is preferable to choose, as a material of the cover sheet according to the invention, commodity material such as polyolefin, cotton and a mixture of polyolefin and cotton or paper. In particular, a preferable material is non-woven web of polyester/pulp having high strength and of low cost which is advantageously used in medical machines and in disposal masks, surgical drapes and surgical gowns.

In the cover sheet according to the invention, the electric conductive area portions corresponding to electrode portions of a body composition measuring apparatus must be electrically conductive. This electric conductive area portions may be formed (1) directly from electric conductive materials, or (2) by subjecting a non-conductive material such as non-woven web or plastic material to so-called electro-conductive treatment. The latter electro-conductive treatment is suitable for mass productive.

In the case (1) in which the electric conductive area portions are made directly from electric conductive material, a cover sheet according to the invention can be produced by making openings in a non-conductive sheet at portions corresponding to the electrodes, placing an electric conductive patch onto the opening and then connecting or securing an outer periphery or an edge of the electric conductive patch to an inner periphery or an edge of the opening with adhesive or by welding. The electric conductive patch can be made of any electric conductive material. In general, the non-woven web can be rendered or changed into electric conductive by two methods. In first method, an electric conductive material is kneaded into (mixed with) a material for the non-woven web and the resulting mixture is spun into filaments or fibers, so that the electric conductive patch is prepared from the resulting electric conductive filaments or fibers. In the second method, commercially available non-woven web is subjected to so-called electric conductive treatment to produce the electric conductive patch. The electric conductive patch may have any shape such as knit, woven fabric, non-woven web and sheet. For example, the electric conductive patch may can be made of textiles and non-woven fabric of fibers or sheets impregnated with electric conductive material. Sheet or textile made of synthetic resign such as polyamide, polyurethane or acetate in which carbon is dispersed may be used as the conductive patch if the cost permits. A non-conductive sheet for forming the non-conductive area portion may be made from any insulation material such as polyethylene and polyester/paper mixture.

In the case (2) in which a non-conductive material is rendered or changed to the conductive area portions by the electric conductive treatment, one can use well-known technique of electric conductive treatment. The insulation area portion may be masked during the electric conductive treatment. A variety of electric conductive materials used in the treatment are also well-known and metal powder such as powder of aluminum, iron, silver and gold or of metal salt or inorganic powder such as carbon powder or carbon fiber are used generally. It is preferable to use electric conductive filler such as carbon black that is relatively cheap and suitable for mass production. In the electric conductive treatment, a solution in which the electric conductive material is dispersed may be applied onto a non-woven web through a pattern sheet having through holes corresponding to electrodes. It may be possible to use a compound that can disperse the electric conductive material uniformly and improve wettability to the non-woven web, such as a solvent (i.e. water, alcohol or ester) containing surface-active agent and salt.

The electric conductive area portions and/or the insulation area portions may be made of laminating material. For instance, an upper surface of insulation area portions may be made of low density polyethylene film and a lower surface may be made of a non-woven web of rubber or elastomer. Although there may be little advantage to make the electric conductive area portions a laminate structure from a viewpoint of improvement in electric conductivity in thickness direction, the electric conductive area portions may be made of a plurality of laminated layers. For instance, the upper surface of electric conductive area portions may be made of polyamide mesh and the lower surface may be made of a non-woven web of electric conductive polyamide. It is also possible to use a variety of laminated combinations such as a combination of antibacterial non-woven web/bacteria impermeability non-woven web or a combination of textile/non-woven web.

The cover sheet according to the present invention can contain other additives such as antibacterial agent, anti-microorganism agent, deodorant, antioxidant, moisture-keeping agent, relaxation agent, freshness-keeping agent, anti-inflammation agent, analgesic agent, or additives acting or contributing for health and beauty and possessing anti-fungus property, anti-allergic action, moisturizing effect and environment atmosphere improving effect such as catechin, sterilization ceramics and borax, or photo catalyst such as titanium oxide, antioxidant and fire retardant.

The cover sheet according to this invention has preferably anti-slip property at least a part of its upper surface and/or lower surface. In particular, slip between the cover sheet and the platform is not desirable for safety. When the cover sheet according to this invention itself possesses an anti-slip property, it can be used safely with no anti-slip treatment on the platform. The anti-slip treatment may be arranged even on the platform by applying a urethane film at least partly for example and in this case, the cover sheet according to this invention having an anti-slip property can be used more safely. The anti-slip property can be imparted also by a property of material itself. In fact, a material such as polyurethane itself can be an anti-slip cover sheet. In case of a non-woven web made of polyethylene, polyester or a mixture with cellulose, it is preferable to effect anti-slip treatment on at least a part, preferably whole surface of the sheet. This anti-slip treatment can be done by any well-known technique such as coating natural or synthetic rubber material, elastomer, silicon rubber or adhesive in a desired pattern such as a dot patter and a line pattern. The anti-slip treatment can be done over whole surface of a sheet, provided that such treatments do not affect measurement.

The anti-slip treatment can be omitted or weakened when the cover sheet is held by the feeding unit and by the collecting unit in the automatic dispenser in which the cover sheet is fed continuously from a stock roll.

It is preferable to indicate or mark the electric conductive area portions on the cover sheet according to this invention, so that operator, user or examinee can easily recognize or confirm, at a glance, locations of the electric conductive area portions and align them to the electrode portions of a measuring apparatus without mistake. For this purpose, it is preferable to print a frame (window) at the electric conductive area portions. It is also preferable to mark a spot for alignment such as center marks and lines indicating installation positions. For instance, feet marks can be printed on a cover sheet according to the invention to facilitate positioning of feet.

Now, actual usage of the cover sheet according to the present invention will be explained with reference to the attached drawings.

Figure 1:
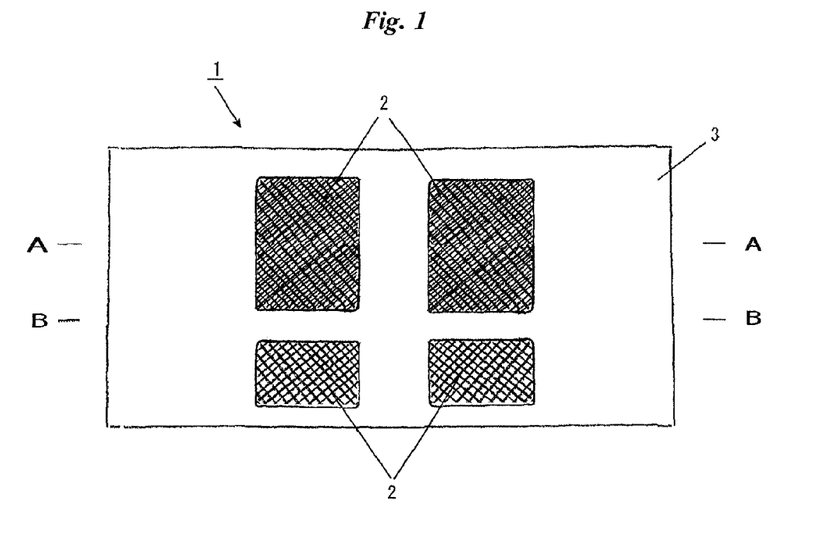
FIG. 1 illustrates a plane view of a cover sheet according to this invention.
Figure 2:
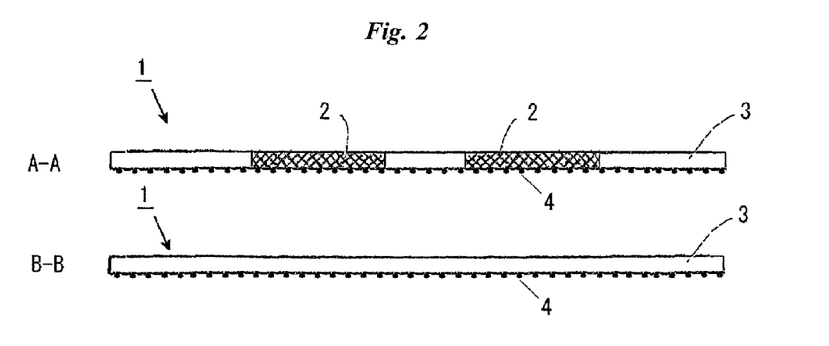
FIG. 2 illustrates a cross-sectional view along cross-sections of A-A line and B-B line in FIG. 1.

FIG. 1 is an illustrative plane view of the cover sheet (1) according to the present invention, and FIG. 2 is an illustrative cross-sectional view along A-A line and B-B line in FIG. 1. This cover sheet (1) comprises electric conductive area portions (2) corresponding to electrode portions of a body composition measuring apparatus and insulation area portions (3) spacing adjacent electric conductive area portions (2). The electric conductive area portions (2) must be electro-conductive along the thickness direction (a direction from bottom to top in FIG. 2). The insulation area portions (3) must have an insulation property at least in planar direction (in a plane of FIG. 1). Anti-slip dots (4) of rubber are formed on a lower surface of the cover sheet (1).

Figure 3A:
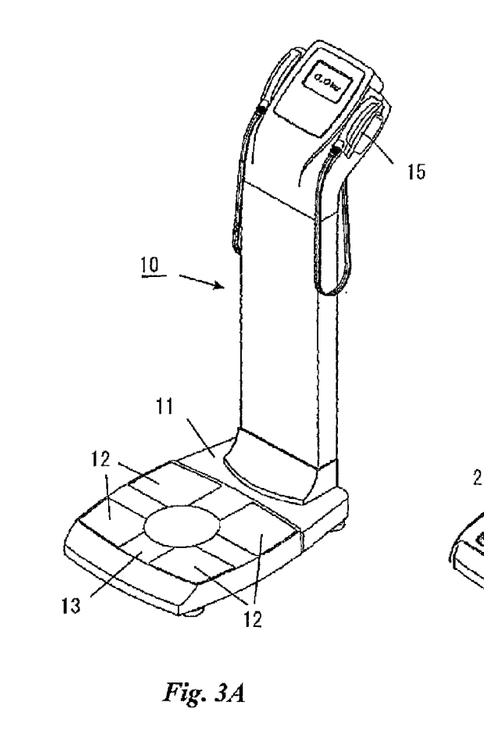
FIG. 3A shows a body composition measuring apparatus using the body impedance technique.

FIG. 3A shows a body composition measuring apparatus (10) using the impedance technology. The body composition measuring apparatus (10) of FIG. 3A is a multi-frequency type body composition measuring apparatus for measuring a body fat percentage, a muscle mass, a water content in body and weight.

Figure 3B:
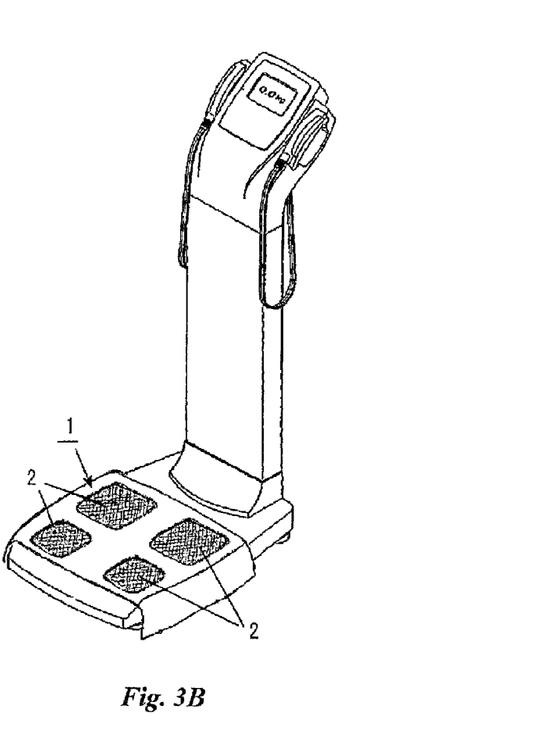
FIG. 3B illustrates an embodiment of a cover sheet according to this invention used in the body composition measuring apparatus shown in FIG. 3A.

FIG. 3B shows an embodiment of a cover sheet (1) according to the present invention used in the body composition measuring apparatus (10) of FIG. 3A. In use, an examinee stands on a platform (11) and holds handset (15) to display a variety of data mentioned above. The platform (11) has electrode portions (12), four portions in this drawing and insulation portions (13) spacing adjacent electrode portions (12).

The cover sheet (1) shown in FIG. 3B according to this invention can be used to prevent a cross-infection via the platform (11) and/or handset (15). The anti-slip treated on the lower surface of the cover sheet (1) make a person on the coversheet (1) safe from slipping.

Figure 4A:
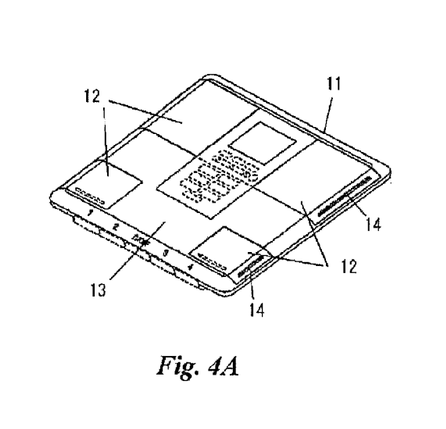
FIG. 4A shows a family type or home use type of a body composition measuring apparatus.
Figure 4B:
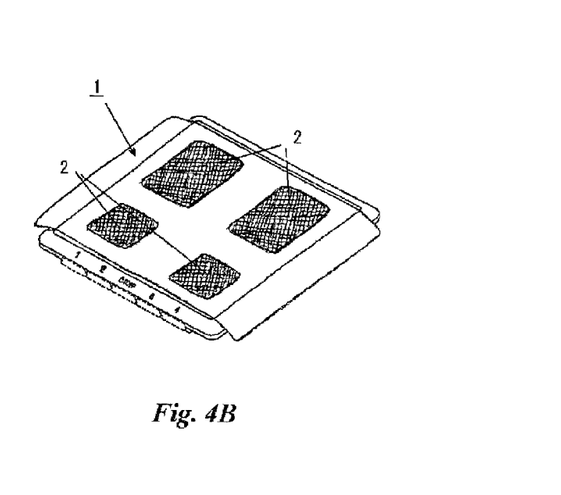
FIG. 4B illustrates another embodiment of the cover sheet according to the invention for the family type body composition measuring apparatus of FIG. 4A.

FIG. 4A shows a family type or home use type body composition measuring apparatus and FIG. 4B shows an embodiment of the cover sheet (1) according to this invention used in the body composition measuring apparatus of FIG. 4A. Reference numbers used in FIG. 4A and FIG. 4B are same as those used in FIG. 3A and FIG. 3B. In FIG. 4A, plane fasteners (14) are secured by double-stick tapes onto the body composition measuring apparatus at suitable positions. In use, the cover sheet (1) made of non-woven web is pressed onto the plane fasteners (14) so that the cover sheet (1) is fixed securely. In family type body composition measuring apparatus, the same cover sheet may be used repeatedly for family members without changing until it gets dirty, therefore in most cases, the labor in changing the cover sheet caused by using the plane fasteners (14) does not matter.

Figure 5A:
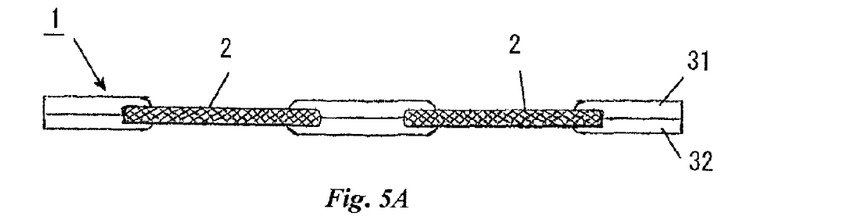
FIG. 5A illustrates a cross-sectional view of a variation of the cover sheet according to invention.

FIG. 5A illustrates a variation of the cover sheet (1) according to this invention. In FIG. 5A, the insulation area portions (3) are made of a laminate. For instance, an upper insulation area portion (31) may be made of a low density polyethylene sheet, while a lower insulation area portion (32) may be made of a urethane sheet. Materials of the upper and lower insulation area portions (31 and 32) can be selected from a variety of plastic materials, paper and elastomers with considering cost, strength, workability and other factors. They can have any desired configurations such as non-woven web, textile, sheet and film. The electric conductive area portions (2) also may be made from a variety of materials like the insulation area portions (13 and 32), provided that the electric conductive areas meet such requirement that they have the electric conductivity along thickness direction.

Figure 5B:
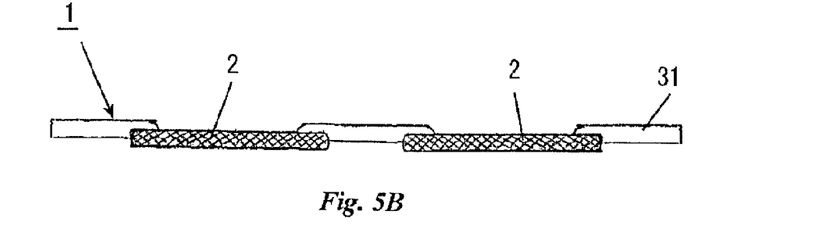
FIG. 5B illustrates a cross-sectional view of further variation of the cover sheet according to invention.

FIG. 5B illustrates a simplified variation of the cover sheet (1) having no lower insulation area portions (32) shown in FIG. 5A. The electric conductive area portions (2) are fixed at their outer periphery to the insulation area portions (31 and 32) with adhesive or by welding.

Figure 6A:
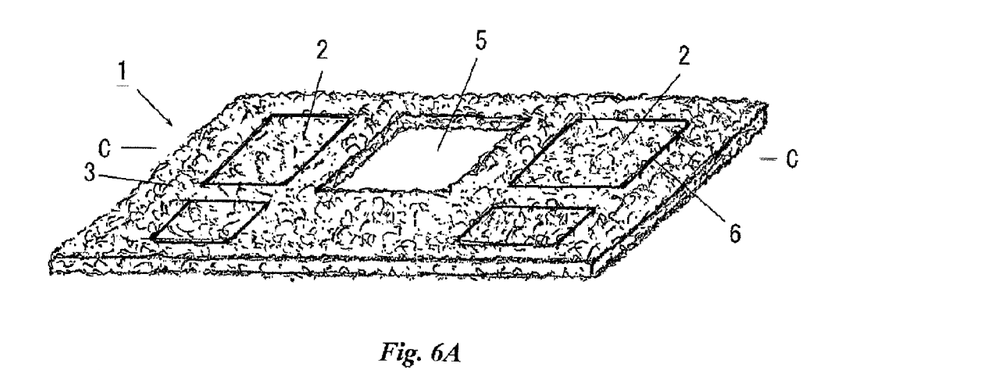
FIG. 6A is an illustrative perspective view of another variation of the cover sheet according to invention.
Figure 6B:
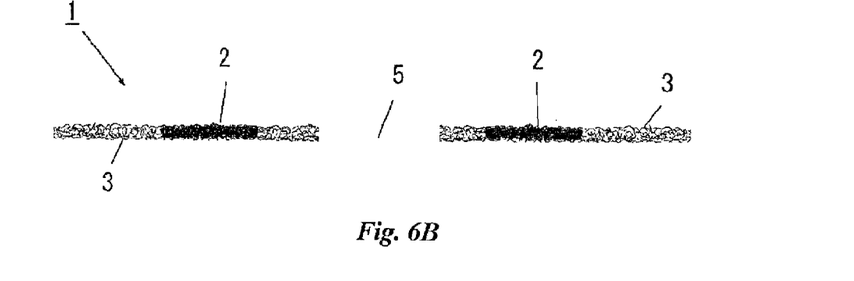
FIG. 6B is a cross-sectional view of the cover sheet of FIG. 6A.

FIG. 6A is a schematic view of another variation of a cover sheet of non-woven web for uses in a family type or home use type body composition measuring apparatus shown in FIG. 4A. To clarify the drawing, a scale in thickness direction is enlarged. FIG. 6A is an illustrative perspective view, while FIG. 6B is an illustrative cross-sectional view along C-C line of FIG. 6A. In this embodiment, electric conductive area portions (2) are prepared by rendering or treating corresponding portions of a non-woven web to electric conductive. In this cover sheet (1), a window (5) is made at a location corresponding to a meter portion in the family type body composition measuring apparatus shown in FIG. 4A so as to read the measured data without difficulties. The window (5) can be covered by a transparent sheet. Marks (6) are printed to indicate the feet setting positions. The marks may indicate the orientation of orientation of left, right, up and bottom. Or, footmarks can be printed so that the cover sheet (1) is not placed at wrong position and/or direction.

Figure 7A:
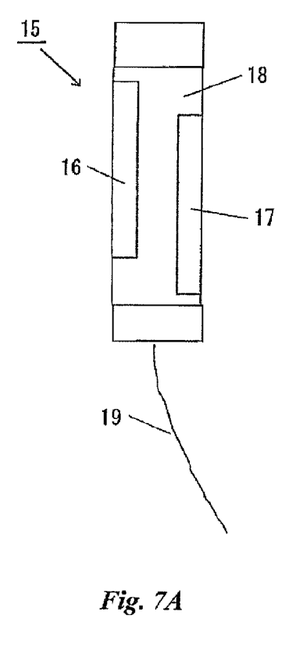
FIG. 7A is an illustrative rear view of a handset used in a body composition measuring apparatus.
Figure 7B:
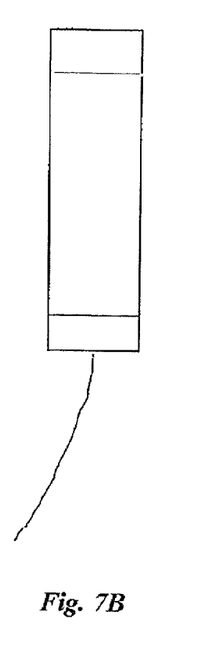
FIG. 7B is an illustrative front view of the handset of FIG. 7A.

FIG. 7A illustrates a handset (15) used in the body composition measuring apparatus (10) shown in FIG. 3A. FIG. 7A is a view of rear surface, while FIG. 7B is a view of front face of the handset (15). The handset (15) has two electrodes (16 and 17) spaced or isolated by insulation portions (18). This handset (15) is connected to a body composition measuring apparatus (10) through a lead wire (19). In use, an examinee standing on the platform (11) holds the handset (15), and the electrodes (16 and 17) function as hand electrodes.

Figure 7C:
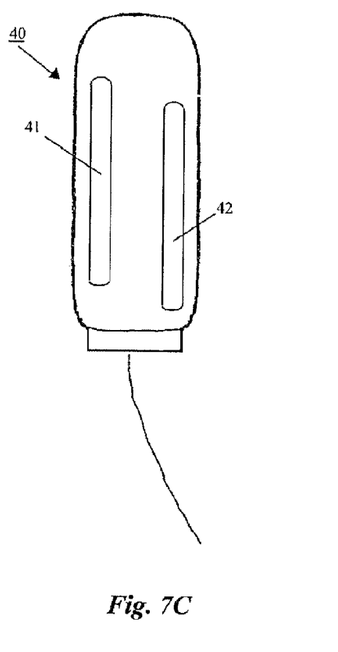
FIG. 7C shows a handset cover fitted on the handset of FIG. 7A.

FIG. 7C illustrates a handset cover (40) fitted over the handset (15). This handset cover (40) can be inserted onto the handset (15) from a free end that is opposite to the lead wire (19). Electric conductive area portions (41 and 42) are formed on the handset cover (40) at the positions corresponding to each electrode. In the drawing, the handset (15) has a square shape in cross-sectional, so that the electric conductive area portions (41 and 42) are positioned at proper positions corresponding to the electrodes (16 and 17) when the handset cover (40) is inserting simply onto the handset (15) since the handset cover (40) has a three-dimensional shape corresponding to that of the handset (15).

In another variation (not shown), the handset cover can be a simple sheet as is shown in FIG. 4B. This sheet may be wound around the handset (15) and is secured at correct position of the handset (15) by plane fasteners (not shown).

The cover sheet according to this invention can be used as a fouling prevention sheet or an etiquette sheet by placing it on a simple body weighing meter having no electrodes.

The cover sheet according to the present invention can be used in a form of unit cover sheet one by one, but it may be much convenient for users that the cover sheets are supplied in a form of a stock in which a plurality of unit cover sheets are connected in series in detachable manner, so that a user can draw each unit cover sheet from the stock as necessary. The stock can be a form of a roll form in which a plurality of unit cover sheets are connected and wound, or in a form of stack like so-called "tissue paper" box in which a plurality of unit cover sheet stacked with nesting partly so that successive two unit cover sheets can be drawn without discontinuity.

In case of the wet type cover sheet, the maker supplies the stock in a form of a set of the stock and a container packing the stock hermetically inside so that users keeps the packed condition until use, to prevent desiccation of the wet type cover sheets. The container may be a plastic bag or box having optionally a barrier layer for humidity and having an opening through which the cover sheet is withdrawn.

Figure 8:
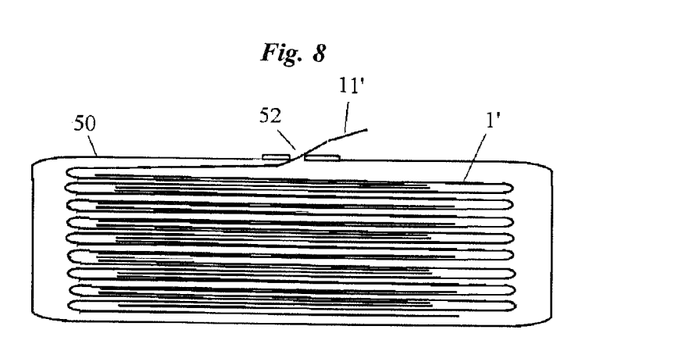
FIG. 8 illustrates an embodiment of a set of a cover sheet stock and a container packing the stock.
Figure 9:
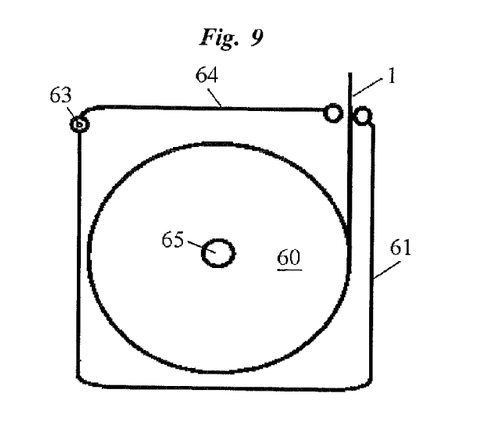
FIG. 9 illustrates another embodiment of a set of a cover sheet stock and of a container packing the stock suitable for "wet type".

FIG. 8 and FIG. 9 illustrate two embodiments of the set according to the present invention, comprising a cover sheet stock and a container packing the stock.

In case of FIG. 8, a plurality of unit cover sheet (1') are stacked alternately like so-called "tissue paper" with nesting partly so that successive two unit cover sheets can be drawn without discontinuity, and a stack of the unit cover sheets (1') is stored in a soft plastic bag (50) having a barrier layer for humidity. FIG. 8 illustrates a state when a leading end (11) of a unit cover sheet (1') is drawn out of an opening (52) formed in the bag (50). In order to avoid desiccation of the wet type cover sheets, a suitable lid (not shown) can be bond or welded around the opening (52).

In case of FIG. 9, a plurality of unit cover sheet (1') are connected in series with detachable manner and wound in a form of a roll shaped stock (60). This stock (60) is stored in a plastic container (61) such as a plastic case. A detaching line such as perforations or easy separable line (not shown) is made between successive two unit cover sheets. When the stock (60) is set in the plastic box (61), a user can turn a lid (64) around a hinge (63). To guide a center core (65) of the roll stock (60), guide grooves (not shown) are formed on inner surfaces of the plastic box (61). A hermetic seal may be arranged at an outlet of the plastic box (61) through which a leading end of the roll stock (60) is drawn.

The cover sheet of this invention can be placed or set on the electrode zones of a body measuring apparatus automatically by using an automatic cover-sheet dispenser. The automatic cover-sheet dispenser is particularly advantageous when many examinees are measured successively in a health center, hospital and complete physical examination. The automatic cover-sheet dispenser may have a feeding unit for the cover sheet arranged at a side of the body measuring apparatus and a collecting unit of the cover sheet at an opposite side.

The automatic cover-sheet dispenser has preferably a feeding unit and a collecting unit of the cover sheet. The feeding unit is equipped with (1) a case for storing a stock in a form of a roll or of stack, and (2) means for drawing the cover sheet out of the stack (such as driving means and guides). The collecting unit is equipped with (3) driving means (such as driving means and guides) for drawing the cover sheet supplied from the feeding unit and (4) a collecting case for collected cover sheet. The automatic cover-sheet dispenser has preferable means for controlling or synchronizing operations of the feeding unit and of the collecting unit, a switch for initiating a feed motion of the cover sheet, and a display showing operation conditions.

The automatic cover-sheet dispenser may have following optional means:
(6) Sensors to detect electro-conductivity, a resistance meter (arranged usually at the feeding unit side),
(7) Indexing means for positioning the cover sheet at a proper position on the electrode zones of the body measuring apparatus (this indexing can be marks printed on the cover sheet that are detected optically),
(8) Means for holding the cover sheet temporally on the electrode zones of the body measuring apparatus with no slip,
(9) Means for feeding water or humidity (in case of wet type cover sheet)

The automatic cover-sheet dispenser according to the present invention can be combined or used together with any existing body measuring apparatus with neither modification nor change thereof.

Figure 10:
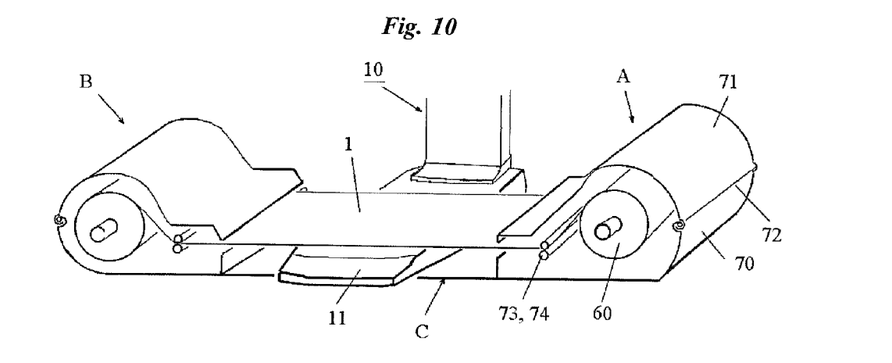
FIG. 10 is an illustrative perspective view of an example of an automatic cover-sheet dispenser according to the present invention, front parts of housings being removed so as to show interiors of the dispenser.
Figure 11:
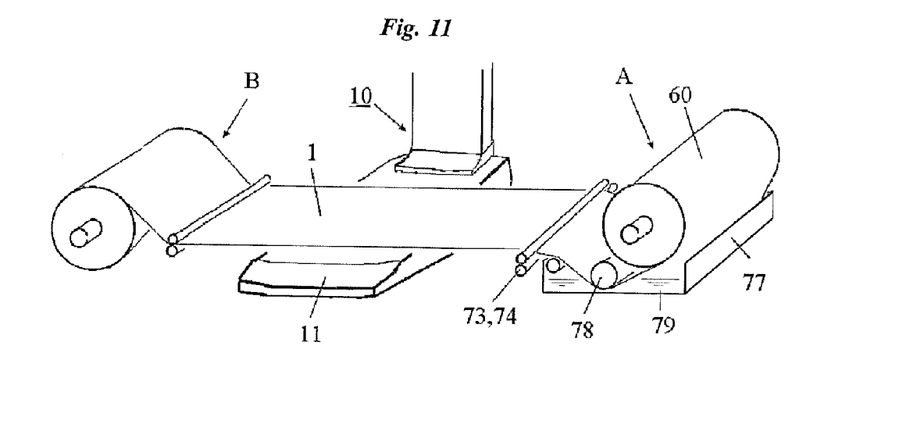
FIG. 11 is a variation of FIG. 10, equipped with a humidifier.

FIG. 10 is an illustrative perspective view of an example of the automatic cover-sheet dispenser according to the present invention. FIG. 10 is a partial cross-sectional view in which front parts of housings are removed to show interiors of the dispenser. FIG. 11 is a variation of FIG. 10.

The automatic cover-sheet dispenser shown in FIG. 10 has a feeding unit (A) and a collecting unit (B) of the cover sheet. Two units (A, B) are connected by a connecting plate (C) which fixes a relative position of the units (A, B). In order to facilitate adaptation of the automatic cover-sheet dispenser to an existing body measuring apparatus, the feeding unit (a), the collecting unit (B) and the connecting plate (C) may be integrated by a simple connecting means (not shown) such as screws or clamps.

A housing of the feeding unit (A) comprises a container (70) for a stock (60) and a container cover (71), which are connected through a hinge (72). In use, a user is requested only to open the container cover (71), to insert a new roll stock (60) in the container (70), to pull out a leading top of a cover sheet from the stock and to place the cover sheet on a plat form (11) of the body measuring apparatus (10), and then to close the container cover (71). The drawn cover sheet is clamped between an upper presser roller (73) supported by the container cover (71) and a lower presser roller (74) supported by the container (70). These presser rollers (73, 74) may be used as terminals of a conductor sensor or of a resistance meter. It is also possible to use a mechanism to drive the presser rollers (73, 74) vertically, so that a clearance between the presser rollers (73, 74) is enlarged when the cover sheet is advanced, and the cover sheet is clamped by the presser rollers (73, 74) during a stage of measurement to prevent slip of the cover sheet (1).

The collecting unit (B) has basically same mechanism as the feeding unit (A). In case of the collecting unit (B), it is necessary to arrange a driver (such as an electric motor) for pulling the cover sheet (1) or for rotating a core shaft around which the cover sheet (1) is wound and a mechanism for connecting the core shaft to the driver. It is preferably to arrange another driver also in the feeding unit (A) and to synchronize motions of two divers.

In the housings of the feeding unit (A) and/or the collecting unit (B), a variety elements or mechanisms (not shown) such as a guide means of the core shaft, a conductor sensor or a resistance meter, a feed mechanism, drivers for the presser rollers (73, 74) and a computer (such as a control board) for controlling all movements in the automatic cover sheet dispenser can be arranged. These elements are not shown in the drawings for clarity.

The automatic cover sheet dispenser shown in FIG. 10 can be used for both type cover sheets of wet type and dray type. To avoid dry-out of the wet type cover sheet, it is advantageous to keep the container cover (71) at a closed position.

FIG. 11 is an illustrative perspective view of another example of the automatic cover-sheet dispenser according to the present invention and is a variation of FIG. 10. In the dispenser of FIG. 11, a feeder of electro-conductive liquid such as water is added to the dispenser of FIG. 10. In FIG. 11, the housings shown in FIG. 10 are not shown for clarity. The electro-conductive liquid (77) such as water is fed to a pan (77). Water may be fed from a portable water tank (not shown) arranged in a housing in the feeding unit (A). Water in the pan (77) may be maintained at a predetermined level.

Figure 12:
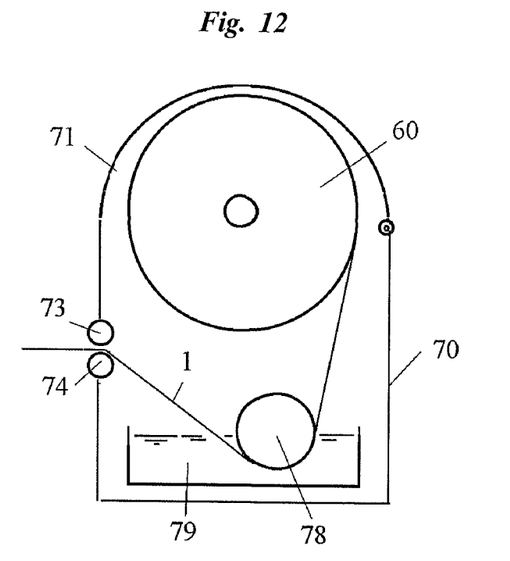
FIG. 12 is an illustrative perspective view of a cover sheet dispenser that is designed for home uses.
Figure 13:
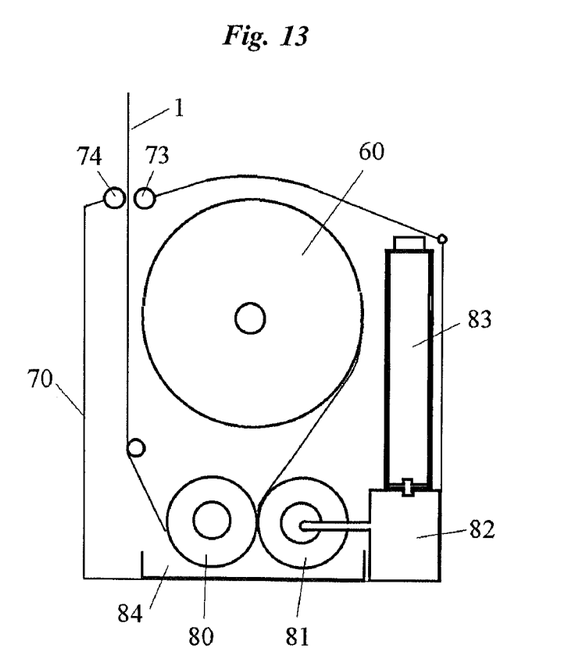
FIG. 13 is an illustrative perspective view of a variation of FIG. 12.

FIG. 12 and FIG. 13 show further another type cover sheet dispensers that are designed for home uses by simplifying and reducing the sized of the dispenser shown in FIG. 11 equipped with a feeder of electro-conductive liquid (such as water). FIG. 12 and FIG. 13 are illustrative cross sections of the feeder of electro-conductive liquid and same reference numbers are assigned to the same or similar parts.

The feeder of electro-conductive liquid shown in FIG. 12 is designed so as to use only the feeding unit (A) of FIG. 11. A container cover (71) has a handle (not shown) for facilitating transportation thereof or to increase its portableness. In use, a user opens the container cover (71), inserts a new roll stock (60) in the container (70), draws a leading end of the cover shoot (1) and passes it under a guide roller (78) immersed in water, and then closes the container cover (71). The cover sheet (1) pulled out is cut along perforations and a separate cover sheet is set on the platform (11) of the body measuring apparatus as is shown in FIG. 3B and in FIG. 4B.

In FIG. 13, water is not fed to the pan (77) but is fed to water feed rollers (80, 81) such as sponge rollers to avoid spillage of water. Water is supplied from a water tank (83) through a feed controller (82) to at least one of the sponge rollers. A shallow pan (84) is arranged to collect dropped excessive water.

This housing also has a handle (not shown) for facilitating transportation thereof or to increase its portableness. In use, a user opens the container cover (71), inserts a new roll stock (60) in the container (70), draws a leading end of the cover shoot (1) and passes it under a sponge roller (80), and then closes the container cover (71). To facilitate changing operation of the roll stock (60), it is desirable to have such a design that a leading end of the cover sheet (1) is passed under the sponge roller (80) when the container cover (71) is opened. In the case of FIG. 13, the cover sheet (1) pulled out is cut along perforations and a separate cover sheet is set on the platform (11) of the body measuring apparatus as is shown in FIG. 3B and in FIG. 4B.

The cover sheet dispensers shown in FIG. 12 and FIG. 13 are suited in particular for home uses of the wet type cover sheet but can be used also for the dry type.

Figure 14:
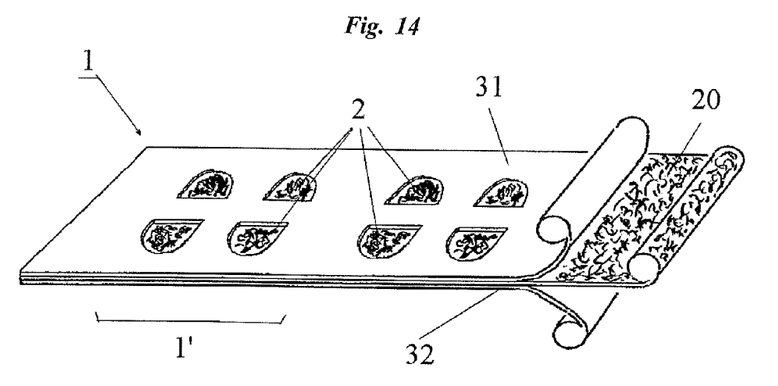
FIG. 14 is an illustrative perspective view of a variation of the cover sheet shown in FIG. 5A.

FIG. 14 is a variation of the cover sheet shown in FIG. 5A and is used mainly for wet type. This cover sheet according to the present invention has a three-layered structure. For example, a non-woven web (20) is sandwiched between opposite surface sheets (31, 32) of insulation material such as low density polyethylene. Zones corresponding to the electric conductive area portions (2) of the surface sheets (31, 32) are punched out to form openings and the non-woven web (20) is appeared at the openings (punched out zones). A difference from the cover sheet of FIG. 5A resides in that the non-woven web (20) is not subjected to electro-conductive treatment. Namely, the cover sheet of FIG. 14 is used in the wet type and electro-conductive liquid is coated, sprayed or adhered onto the electric conductive area portions (2) to create the electro-conductive property, at usage for example. In fact, only the electro-conductive liquid sprayed gives the electric conductivity in thickness direction. The non-woven web (20) can be connected to the surface sheets (31, 32) of low density polyethylene by adhesive or welding.

If necessary, insulation of the surface sheets of low density polyethylene can be assured by effecting such a treatment that the electro-conductive liquid do not penetrate into other parts of the electric conductive area portions (2) in the non-woven web (20). For example, a zone preventing penetration of electro-conductive liquid can be arranged at the centerline or zone of the non-woven web (20). In practice, a water-repellent line is coated or welded on the non-woven web (20) along its longitudinal centerline, or a material of the non-woven web (20) is replaced by water-impermeable or water-repellent material along its longitudinal centerline or zone. In the same manner, it is possible to effect similar treatment that prevent penetration of the electro-conductive liquid of the cover sheet (1) along transverse direction (from bottom to top direction in FIG. 14)

There is no serious problem even if the surface sheets (31, 32) contain a small amount of electro-conductive liquid. In fact, a distance between electrodes in a plane direction is very longer than a thickness, so that electric resistance of the surface sheets (31, 32) in the plane direction is high and gives no influence to measurement. If necessary, a calibration table can be added to a measuring circuit.

Figure 15:
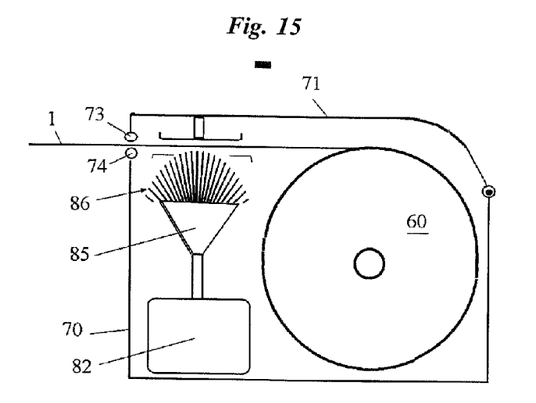
FIG. 15 is an illustrative cross section of another type of a cover sheet dispenser designed for the variation of FIG. 14.

FIG. 15 is an illustrative cross section of a device used to coating, spraying or adhering electro-conductive liquid onto the cover sheet shown in FIG. 14. In FIG. 14, same reference numbers are assigned to the same or similar parts shown in FIG. 12 and in FIG. 13. A difference from FIG. 13 resides in that the water feed roller is replaced by a spray nozzle (85). A pattern plate having perforation patterns corresponding to the electric conductive area portions (2) (not shown) can be arranged between the cover sheet (1) and the spray nozzle (85), so that a spray (86) of the electro-conductive liquid such as an aqueous solution is limited to the electric conductive area portions (2). It is also possible to synchronize a timing of spraying with a feed speed of the cover sheet, and to use a more than two spray nozzles or to arrange the spray nozzle at opposite side of the cover sheet.

Devices shown in FIG. 12 and FIG. 13 also can be used to effecting coating, adhesion or spraying of the electro-conductive liquid onto the non-woven web (20) shown in FIG. 14.

Now, embodiments of the present invention will be explained.

EXAMPLE

Embodiment 1

On a sheet (3) of low density of polyethylene, four square opening, each having a dimension of 13 mm×13 mm, were made at positions corresponding to the area portion of "2" in FIG. 3B. Four square electric conductive patches (2) of 15 mm×15 mm were cut from an electric conductive non-woven web (thickness of 0.3 mm) in thickness direction consisting of commercially available polyester/paper. Each square electric conductive patch of the electric conductive non-woven web (2) was secured at its outer periphery onto each square opening of sheet (3) of low density of polyethylene with adhesive or a heat seal to obtain a cover sheet according to this invention having a structure shown in FIG. 5B. Resistance values of the square patches of electric conductive non-woven web (2) along thickness direction were in a range of from 400 to 500 ohm.

A platform of a body composition measuring apparatus commercially available from applicant in the name of MC-180 was covered with this cover sheet and the body fat of an examinee was measured. For comparison, data without the cover sheet were also obtained. It was possible to cancel a difference in measured results obtained when the cover sheet was used and when the cover sheet was not used, by effecting compensation of data obtained.

Embodiment 2

The same operation as Embodiment 1 was repeated, with using a commercially available electric conductive polyurethane foam sheet (thickness under no compression; 5 mm, and thickness under 40 kg weight; 0.3 mm) instead of the square patch of electric conductive non-woven web (2). Resistance value along thickness direction of the square electric conductive web (2) was several ohms.

The cover sheet was evaluated by the same method as Embodiment 1. In this case, measured result could be used without compensation.

Embodiment 3

The same operation as Embodiment 2 was repeated, with using a textile made of electric conductive polyamide fibers as the square patch of electric conductive non-woven web (2). Resistance value along thickness direction of the square electric conductive web (2) was several ohms.

The cover sheet was evaluated by the same method as Embodiment 1. In this case, measured result could be used without compensation.

Embodiment 4

A cover sheet according to this invention was prepared by subjecting a non-woven web of a polypropylene to electric conductive treatment.

An electric conductive paint was coated onto a commercially available non-woven web of polypropylene at limed areas corresponding to the electric conductive area portion in FIG. 6A, in such a manner that the electric conductive paint penetrated through the non-woven web of a polypropylene from top to bottom. The electric conductive paint was prepared by mixing 100 parts by weight of pulverized silver powders having an average parcel diameter of 50 micro meter and an apparent density of 0.03 gram/cm$^3$ obtained by crushing silver foils having an average thickness of 0.2 micro meter, 1000 parts by weight of acrylic resign and 3000 parts by weight of toluene for 10 minutes. The electric conductive paint was applied onto the non-woven web of propylene and passed through the web from top to bottom. The specific resistance measured after drying was such excellent value as $7 \times 10^{-4}$ Ω-cm in electric conductivity.

The cover sheet was evaluated by the same method as Embodiment 1 and found that the measuring result could be used without compensation.

Anti-slip dots of rubber were printed (diameter of dot is about 1 to 3 mm, space between dots is about 1 cm) on a lower surface of the insulation area portion (3) of the non-woven web. No slip was observed when the obtained cover sheet was placed on a platform (11) of the body composition measuring apparatus (10).

Embodiment 5

Wet Type Cover Sheet for Home Uses

A roll stock (60) of the cover sheet according to the present invention was prepared by using a patch (13 mm×13 mm, a thickness of 1 mm under non-compressed condition) of non-woven web of rayon and pulp blend for the electric conductive patches (2) and a film of low density polyethylene (thickness of 15 to 40 μm) for the insulation area portions (31, 32) shown in the cross section of FIG. 5A. Outer periphery of the patch was heat-welded onto an inner periphery of an opening made in the film of low density polyethylene.

The resulting cover sheet was immersed in an aqueous solution in which water-keeping agent; antibacterial agent and perfume were dissolved so that the rayon-pulp blend fabric, absorbed the solution. Water remained on the low density polyethylene film was removed by passing the cover sheet through a water-suction rollers. Then, the cover sheets were wound in a roll stock.

The roll stock (60) has a width of 430 mm, a length of about 27 m and contained hundred units cover sheets (1') (each having a dimension of 430×450 mm). Perforations, which were tearable by hands, were formed between successive two unit cover sheets.

The patch of non-woven web of rayon-pulp blend absorbing the solution showed nearly zero resistance.

Embodiment 6

Wet Type Cover Sheet for Complete Physical Examination

A roll stock (60) of the wet type cover sheet was prepared by the same process as Embodiment 5. In this case, however, the tearable perforations were not formed because the cover sheets are not cut. A space between successive two unit cover sheets (1') (430×450 mm) was reduced. The total length of hundred unit cover sheets was 450 m.

The resulting roll stock can be used without trouble in the automatic cover-sheet dispenser of the cover sheet shown in FIG. 10.

It should be understood that the present invention should not be limited to Embodiments of described above but persons skilled in the arts can improve, modify and change the Embodiments without deviating from the scope of the present invention.

The invention claimed is:

1. A disposable cover sheet detachably used in a body measuring apparatus comprising electrodes providing an apparatus body thereof for supplying an electric current to a human body or for measuring a difference in electrical potential between two sites of the body, wherein said disposable cover sheet (1) comprises electric conductive area portions (2) corresponding to said electrodes providing said apparatus body of said body measuring apparatus and having an electric conductivity through a thickness direction from an innermost surface to an outermost surface of the cover sheet, and insulation area portions (3) spacing said electric conductive area portions (2) and having an electrically insulating property at least along a plane direction, wherein said disposable cover sheet (1) possesses an anti-slip property at least on a part of said disposable cover sheet (1).

2. A disposable cover sheet detachably used in a body measuring apparatus comprising electrodes providing an apparatus body thereof for supplying an electric current to a human body or for measuring a difference in electrical potential between two sites of the body, wherein said disposable cover sheet (1) comprises electric conductive area portions (2) corresponding to said electrodes providing said apparatus body of said body measuring apparatus and having an electric conductivity through a thickness direction from an innermost surface to an outermost surface of the cover sheet, and insulation area portions (3) spacing said electric conductive area portions (2) and having an electrically insulating property at least along a plane direction, wherein said electric conductivity in the thickness direction of said electric conductive area portions (2) is created by impregnating, adhering or applying electro-conductive liquid into and/or onto a sheet material.

3. The disposable cover sheet according to claim 2, wherein said electro-conductive liquid is an electro-conductive aqueous solution.

4. The disposable cover sheet according to claim 2, wherein said disposable cover sheet (1) is made of non-woven web or fabric, fiber web, felt, textile, knitting or film.

5. The disposable cover sheet according to claim 2, wherein said body measuring apparatus comprises a body composition measuring apparatus comprising four electrodes in order to measure a body composition using the body impedance technique, and said disposable cover sheet (1) including four electric conductive area portions (2) corresponding to said four electrodes of said body composition measuring apparatus.

6. The disposable cover sheet according to claim 5, wherein said body composition measuring apparatus comprises said four electrodes on a platform (11) thereof, where feet bottoms of an examinee contact, and said disposable cover sheet (1) is configured to be placed on said platform (11) in such a manner that said four electric conductive area portions (2) are positioned on said four electrodes of said body composition measuring apparatus, respectively.

7. The disposable cover sheet according to claim 2, wherein said body measuring apparatus comprises a body composition measuring apparatus comprising four electrodes in order to measure a body composition using the body impedance technique, at least two electrodes of said four electrodes of said body composition measuring apparatus are hand electrodes (15) with which hands of an examinee contact, said disposable cover sheet (1) is configured to cover said hand electrodes (15) in such a manner that said electric conductive area portions (2) are positioned on said at least two electrodes, respectively.

8. The disposable cover sheet according to claim 2, wherein said electric conductive area portions (2) and/or said insulation area portions (3) are prepared from non-woven web.

9. The disposable cover sheet according to claim 2, wherein said electric conductive area portions (2) and/or said insulation area portions (3) are prepared from a laminated material.

10. A stock of the disposable cover sheet (1) according to claim 2, wherein said stock comprises a plurality of unit cover sheets (1') connected in series.

11. The stock according to claim 10 in a form of a roll.

12. A set of the stock of the disposable cover sheet (1) according to claim 10, and an openable container (70, 71) packing said stock inside.

13. A stock of the disposable cover sheet (1) according to claim 2, wherein said stock comprises a plurality of unit cover sheets (1') stacked one over other in partly nested manner.

14. The disposable cover sheet according to claim 2, wherein removal of the cover sheet does not affect operation of the body measuring apparatus.

15. A set of disposable cover sheets detachably used in a body measuring apparatus comprising electrodes providing an apparatus body thereof for supplying an electric current to a human body or for measuring a difference in electrical potential between two sites of the body, wherein each said disposable cover sheet (1) comprises electric conductive area portions (2) corresponding to said electrodes providing said apparatus body of said body measuring apparatus and having an electric conductivity through a thickness direction from an innermost surface to an outermost surface of the cover sheet, and insulation area portions (3) spacing said electric conductive area portions (2) and having an electrically insulating property at least along a plane direction, wherein each said disposable cover sheet (1) is made of wet type cover sheet in which said electric conductivity in the thickness direction is created by impregnating, adhering or applying electro-conductive liquid into and/or onto a non-woven web or textile, fiber web or film.

16. An automatic cover-sheet dispenser of disposable cover sheets detachably used in a body measuring apparatus comprising electrodes providing an apparatus body thereof for supplying an electric current to a human body or for measuring a difference in electrical potential between two sites of the body, wherein each said disposable cover sheet (1) comprises electric conductive area portions (2) corresponding to said electrodes providing said apparatus body of said body measuring apparatus and having an electric conductivity through a thickness direction from an innermost surface to an outermost surface of the cover sheet, and insulation area portions (3) spacing said electric conductive area portions (2) and having an electrically insulating property at least along a plane direction, comprising a feeding unit (A) of said disposable cover sheet (1) arranged at a side of the electrodes of said body measuring apparatus, a collecting unit (B) of said disposable cover sheet (1), and means (77-79, 80-84) for feeding electro-conductive liquid.

17. The automatic cover-sheet dispenser according to claim 16, wherein said disposable cover sheet (1) is stocked in a form of a roll or a stack in said feeding unit (A).

18. A method of preventing fouling of a body composition measuring apparatus comprising a plurality of electrodes on a platform (11) thereof, where feet bottoms of an examinee contact, in order to measure a body composition using a body impedance technique, comprising:

covering said platform (11) of said body composition measuring apparatus with a disposable cover sheet comprising a plurality of electric conductive area portions (2) corresponding to said plurality of electrodes of said platform (11) of said body composition measuring apparatus and having an electric conductivity in a thickness direction, and insulation area portions (3) spacing said plurality of electric conductive area portions (2) from one another and having an electrically insulating property at least along a plane direction, said disposable cover sheet comprising anti-slip treatment arranged on at least part of an upper surface and/or a lower face thereof.

\* \* \* \* \*